US00PP13080P2

(12) United States Plant Patent
Hansen

(10) Patent No.: US PP13,080 P2
(45) Date of Patent: Oct. 15, 2002

(54) HOSTA PLANT NAMED 'TOUCH OF CLASS'

(75) Inventor: Hans A. Hansen, Waseca, MN (US)

(73) Assignee: Shady Oaks Nursery LLC, Waseca, MN (US)

( * ) Notice: Subject to any disclaimer, the term of this patent is extended or adjusted under 35 U.S.C. 154(b) by 0 days.

(21) Appl. No.: 09/454,949

(22) Filed: Dec. 3, 1999

(51) Int. Cl.[7] ..... A01H 5/00
(52) U.S. Cl. ..... Plt./353

(58) Field of Search ..... Plt./353

*Primary Examiner*—Bruce R. Campell
*Assistant Examiner*—Michelle Kizilkaya
(74) *Attorney, Agent, or Firm*—Vidas, Arrett & Steinkraus, P.A.

(57) ABSTRACT

A distinct cultivar of Hosta plant named 'Touch of Class', characterized by a unique variegation pattern with relatively wide dark-green margins and light-yellow centers. The new Hosta including clusters of relatively large white flowers having pale lavender centers positioned above the foliage.

2 Drawing Sheets

BACKGROUND OF THE INVENTION

The present invention relates to a new and distinct cultivar of Hosta plant, botanically known as Hosta, cultivar name, 'Touch of Class'.

The new cultivar was selected as a chemically induced mutation by the inventor of the non-patented Hosta hybrid 'June' (unpatented) in about June of 1995 in Waseca, Minn., United States of America.

Asexual propagation of the new cultivar was in 1999 at Waseca, Minn., The United States of America, by division and tissue culture has shown that the unique features of this new Hosta plant are stable and reproduced true to type in successive generations of asexual propagation.

BRIEF SUMMARY OF THE INVENTION

The following traits have been repeatedly observed and are determined to be the unique characteristics of 'Touch of Class'. These characteristics in combination distinguish the new Hosta as a new and unique cultivar:

1. Medium sized, heavily substanced cordate leaves which tend to be more pointed and wedge shaped when the plant is mature comprising a compact small to medium to sized plant mound;

2. Yellow centered leaves with a very wide uneven blue margin which comprises approximately two-thirds of the leaf area, the leaves having an apparent third color, that may be yellow-green to green in apparent color where the margin and center colors meet; and 3. Relatively large pale lavender flowers are presented above the foliage in late-summer.

The new Hosta can be compared to its parent cultivar, 'June'. In the new Hosta the variegation pattern has a much more pronounced and substantial margin than in the Hosta 'June'. The yellow center of the new Hosta is reduced proportionally to the increased size of the margin. In addition, the new Hosta bears flowers which are noticeably larger than the flowers of the parent cultivar.

The new Hosta cultivar has not been observed under all possible environmental conditions. The phenotype may vary to some extent with variations in environmental conditions such as temperature and light intensity, without any variance in genotype.

BRIEF DESCRIPTION OF THE PHOTOGRAPHS

The accompanying colored photographs illustrate the overall appearance of the new cultivar, showing the colors as true as is reasonably possible to obtain in colored reproductions of this type.

The first sheet of photographs comprises a top perspective view of a typical plant of the new Hosta, and a close-up view of a typical leaf of the new Hosta.

The second sheet of photographs illustrates for comparative purposes a side view of the larger flower of the of 'Touch of Class' on the left and the relatively smaller flower of the parent cultivar 'June' on the right. Also, for comparative purposes a front view of the larger flower size of the of 'Touch of Class' on the left and the relatively smaller sized flower of the parent cultivar 'June' on the right.

Leaf and flower colors in the photographs may appear differently from the actual colors due to light reflectance.

DETAILED DESCRIPTION OF THE INVENTION

In the following description, color references are made to The Royal Horticulture Society Colour Chart except where general terms of ordinary dictionary significance are used. The following observations and measurements describe three-year old plants, as depicted in the accompanying color photographs, which were grown outdoors in Waseca, Minn., United States of America.

Botanical classification: Hosta, result of chemically induced mutation.
Parentage: Hosta with cultivar name 'June'.
Propagation:
*Method*.—By division and tissue culture.
Plant description:
*Plant shape*.—Compact, dome-shaped.
*Growth habit*.—Initially upright when young, with leaves outwardly arching as they mature.
*Culture*.—Light to medium shade in moist soil.
*Plant type*.—Herbaceous perennial.

*Plant height*.—About 7 inches from soil level to top of leaf plane.

*Plant diameter*.—About 16 inches.

*Vigor and growth rate*.—Slow to moderate.

*Disease resistance*.—No known particular resistance or susceptibility to disease known to Hosta observed.

*Foliage description*.—Leaf shape: Broadly cordate with immature leaves being more wedge shaped. Leaf margin: Entire. Leaf texture: Very heavy, good substance with leaves that are fairly smooth with the exception of ridges formed by the leaf veins. Leaf size: Length: About 5.5 inches. Width: About 4.5 inches. Venation pattern: Campylodrome with 11 pairs of veins. Leaf color: Centers: light yellow (about 2D) Margins: Blue-green, about 114D in the spring changing to 114B by mid-summer, margins being ½ of an inch to 2 inches wide. A third color appears on the leaf where the margins and centers overlap, the third color may range in from Yellow-green (about 144A) to Green (about 138A).

Petioles description: In a mature plant petioles may have a length of approximately 25–30 centimeters in and a diameter of about 1 cm to about 2 cm. The petiole has a central region having light yellow color (about 2D) with a margin having a blue-green color (about 114D).

Flower description:

*Bloom period*.—Mid-summer.

*Fragrance*.—No observed fragrance.

*Flower arrangement*.—Raceme of numerous single flowers comprised of six tepals. The number of flowers per raceme varies from about 23 to about 32 with an average of about 28, with each flower lasting approximately 1 day.

*Flower shape*.—Funnel-shaped.

*Flower scape*.—12–17 inches.

*Flower color*.—Nearly white with pale lavender (about 82D) centers to the interior of the flower petals.

Scape description:

*Number*.—The number of scapes per plant is dependent on the maturity of the plant. Each mature eye comprising the clump may produce a flower scape under normal growing conditions.

Description of reproductive organs: The reproductive organs comprise six stamens and a compound ovary having three locules. The size of the anther is approximately 0.5 cm with a color of about 11A though this may vary to light orange or orange. The pollen is average to moderate in abundance. The stigma is a three lobed stigma of color 155C with a length ranging from about 5 cm to about 8 cm, and the style has a color of about 155A.

Seed development: Has not been observed.

Root development: From transfer to rooting media in tissue culture, rooting takes approximately 4 weeks at about 68 degrees Fahrenheit. After transfer from stage III in tissue culture to planting into soil in a green house, a well rooted plant is produced in approximately 8 weeks with a day time temperature of about 68 degrees Fahrenheit (about 65 degrees Fahrenheit at night) and a soil temperature of about 78 degrees Fahrenheit.

I claim:

1. A new and distinct cultivar of Hosta plant named 'Touch of Class', as illustrated and described.

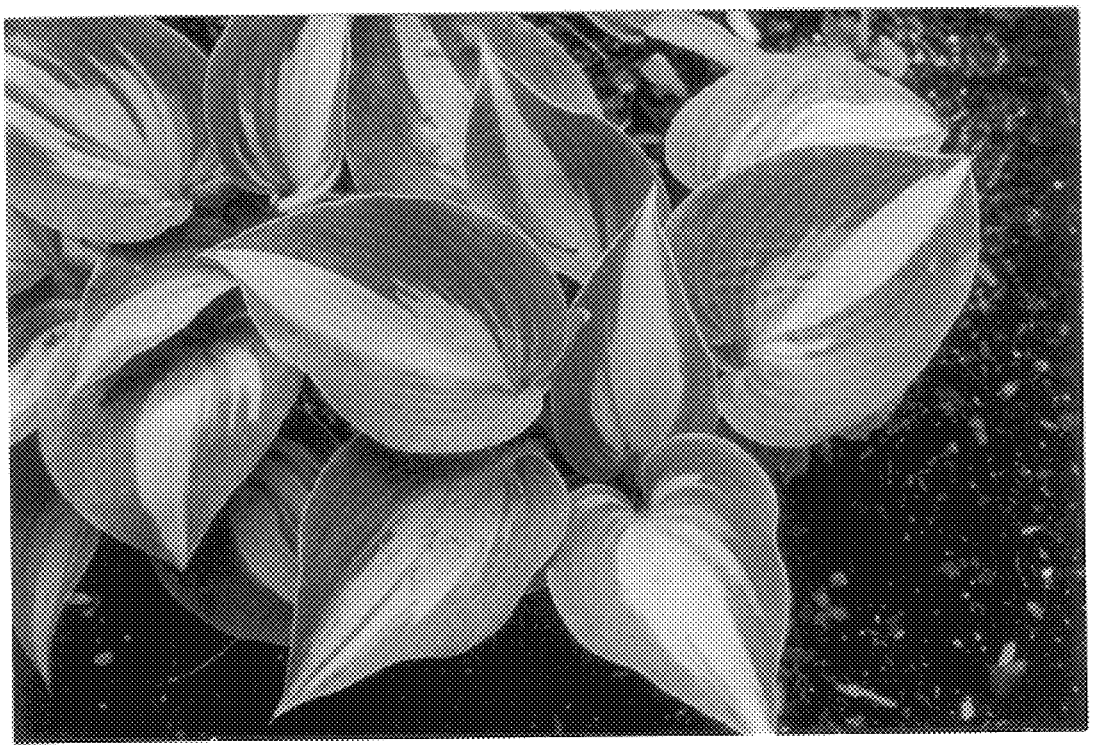
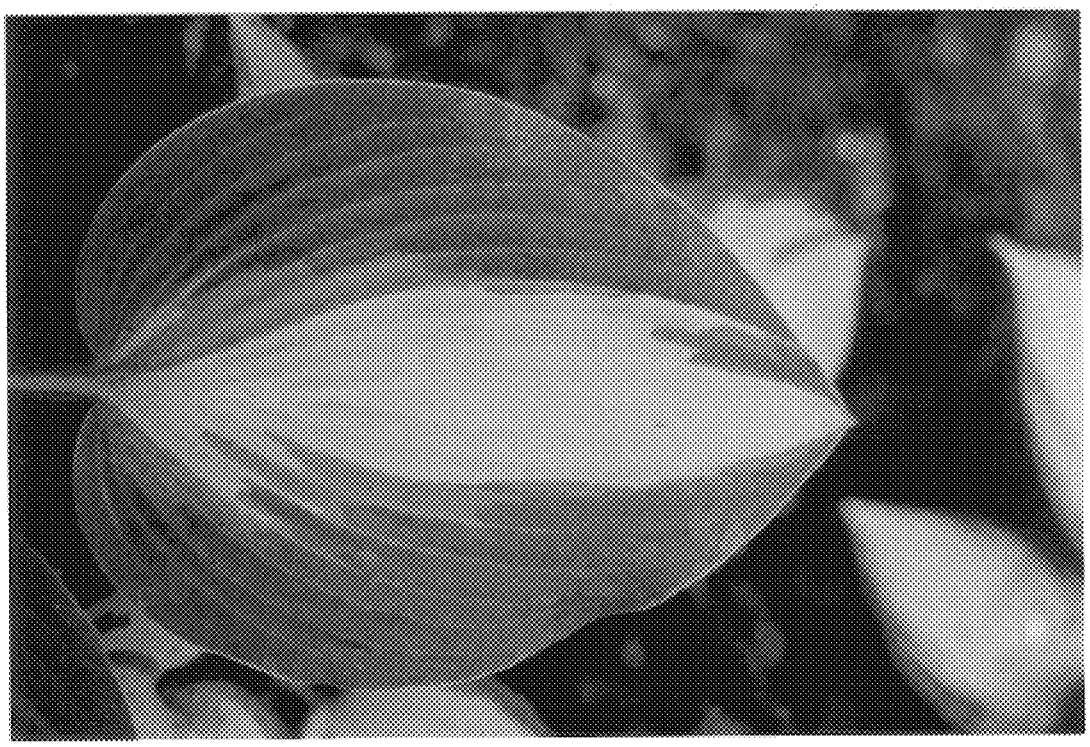

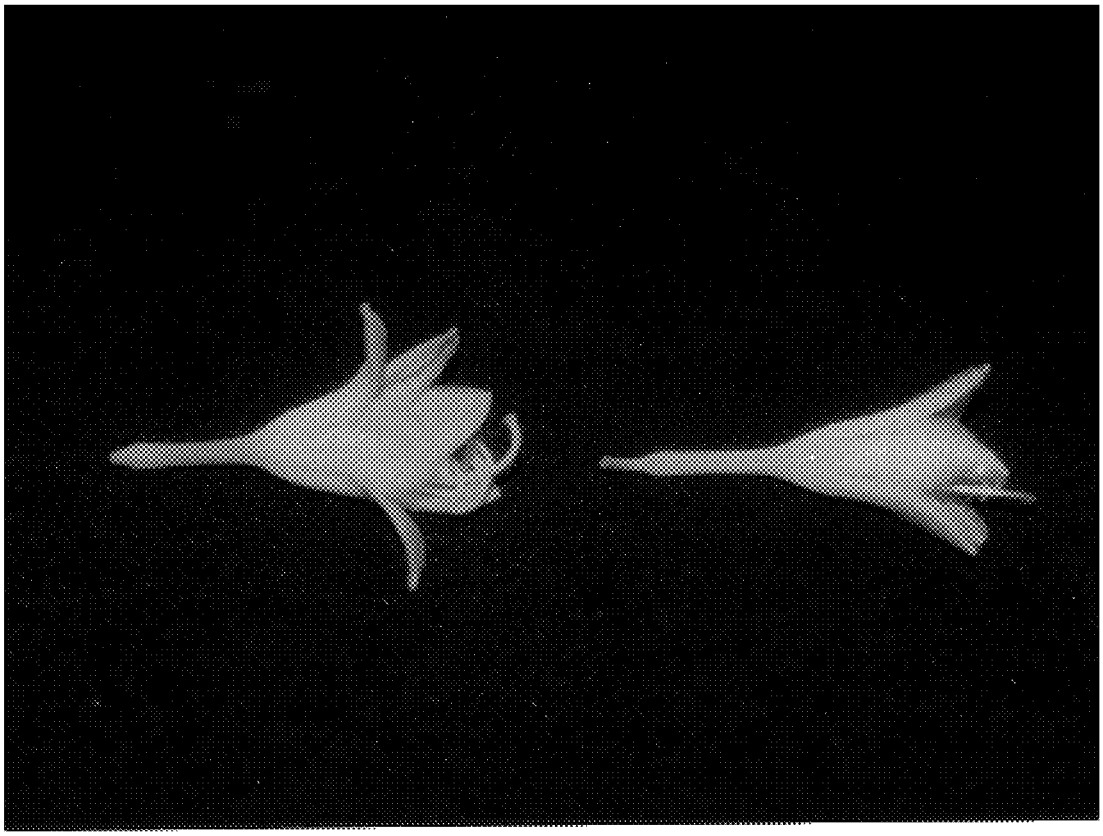
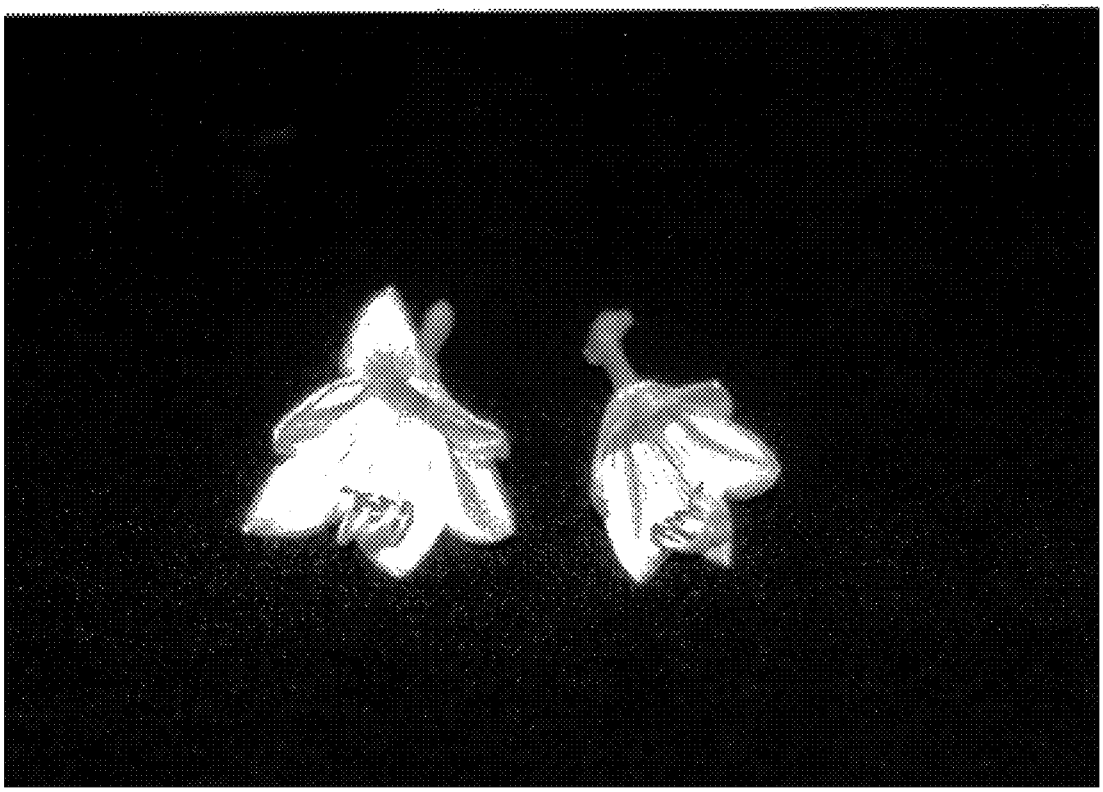

* * * * *